United States Patent [19]

Strimling

[11] Patent Number: 4,468,177
[45] Date of Patent: Aug. 28, 1984

[54] DIAPHRAGM PUMP ARRANGEMENT IN WHICH ALTERNATELY EXPANDED AND CONTRACTED CHAMBERS ARE USED INDEPENDENTLY

[76] Inventor: Walter E. Strimling, 63 Westcliff Rd., Weston, Mass. 02193

[21] Appl. No.: 257,752

[22] Filed: Apr. 27, 1981

[51] Int. Cl.³ .................. F04B 17/04; A61F 1/00
[52] U.S. Cl. ............................ 417/413; 3/1.7; 128/1 D; 417/418
[58] Field of Search ............ 417/413, 418; 3/1.7; 604/152; 128/1 D

[56] References Cited

U.S. PATENT DOCUMENTS

| | | | |
|---|---|---|---|
| 2,930,324 | 3/1960 | Toulmin, Jr. ................ | 417/413 |
| 3,327,633 | 6/1967 | Duinker et al. ............. | 417/418 X |
| 3,422,765 | 6/1969 | Schoch ........................ | 417/418 |
| 3,514,218 | 5/1970 | Maher, Jr. ................... | 417/418 X |
| 3,606,592 | 9/1971 | Madurski et al. ........... | 417/413 |
| 3,754,154 | 8/1973 | Massie ......................... | 417/418 |
| 4,221,548 | 9/1980 | Child .......................... | 417/418 |

FOREIGN PATENT DOCUMENTS

| | | | |
|---|---|---|---|
| 605833 | 7/1948 | United Kingdom ........ | 417/413 |
| 2070148 | 9/1981 | United Kingdom ........ | 417/418 |

Primary Examiner—Leonard E. Smith
Attorney, Agent, or Firm—Bromberg, Sunstein & McGregor

[57] ABSTRACT

A pump has a housing that is divided into two chambers by an element that is driven in a push-pull manner so that the volumes of each of the two chambers are alternately enlarged and reduced. Both chambers are in the path of fluid through the pump.

The chambers of a diaphragm pump in a preferred embodiment are defined by a piston with a hollow annular shape having a magnetic rod secured at its center. The piston travels along the axis of the rod to seat against the conforming surfaces of a hollow housing. The chambers are isolated by a flexible annular diaphragm secured to the piston and a center line of the housing. When adapted as an artificial heart, both chambers fill with blood, one being connected between veins and the lungs, the other being connected between the lungs and arteries.

6 Claims, 5 Drawing Figures

DIAPHRAGM PUMP ARRANGEMENT IN WHICH ALTERNATELY EXPANDED AND CONTRACTED CHAMBERS ARE USED INDEPENDENTLY

DESCRIPTION

Technical Field

This invention relates to gas or fluid pumps and more particularly, for example, to diaphragm pumps which are adaptable for use as a human heart.

BACKGROUND OF THE INVENTION

Diaphragm pumps are well known in the art. Characteristic of such pumps is a housing separated into first and second chambers by a diaphragm. In some instances the diaphragm comprises a rigid central disk portion and a flexible annular portion about the disk. The diaphragm is attached to the housing in a manner to seal the two chambers. Electromagnetic means causes cyclical displacement of the diaphragm alternately expanding and reducing the volume of the chambers reciprocally in a push-pull mode of operation. Each chamber is equiped with an inlet and outlet conduit including check valves operative to admit and eject fluids in the appropriate phases of operation. Displacement of the diaphragm in a first direction increases the volume of one of the chambers in a manner to draw fluid into the chamber through an inlet valve. Displacement of the diaphragm in the opposite direction thereafter reduces the volume of that same chamber, and causes fluid therein to be expelled through an outlet valve.

One problem with such arrangements is that the operation of a diaphragm pump usually requires a second gaseous or liquid medium, other than the gas or liquid being pumped, on one side of the diaphragm. This second gaseous or liquid medium needs venting. Such a requirement for venting precludes the use of a sealed exterior surface of such a pump in submersed or otherwise hostile environments as would occur if used in space or as a heart replacement in an animal or human.

A second problem with such arrangements is that any diaphragm material has a finite permeability. This permeability permits some small portion of the fluid on each side of the diaphragm to reach the other side of the diaphragm, resulting in loss of a small part of the fluid being pumped, and contamination of the fluid being pumped.

A third problem with such arrangements is that any material being used as a diaphragm will crack or rupture when subjected to sufficient pressure and flexing. When such a crack or rupture occurs the gas or fluid on each side of the diaphragm is contaminated by mixing with the gas or fluid on the other side.

SUMMARY OF THE INVENTION

In accordance with the invention, there is provided a pump having a housing that is divided into two chambers by an element that is driven in a push-pull manner so that the volumes of each of the two chambers are alternately enlarged and reduced. Both chambers are in the path of fluid through the pump.

A preferred embodiment of the present invention employs a sealed hollow donut-shaped envelope piston with a rod-shaped electromagnet secured within the central hole defined by the donut and sealing the donut into an inaccessible volume. The donut resides within a likeshaped sealed rigid housing having a median line. An annular-shaped diaphragm is secured to the periphery of the donut and to the median line of the housing and divides the housing into two chambers. Inlet and outlet conduits to each of the two chambers of the pump are connected to sources of the same kind of fluid so that no second fluid is necessary in one of the chambers. For use as an artificial heart, blood occupies both chambers, thus obviating the use of a second fluid and the need for venting. Each chamber is a component part of an isolated circulating system, as is true of the human heart. The solution to the above problems thus arises from the cooperation of the pump and its interconnections to introduce a like fluid into both sides of the pump. The arrangement also permits series connection of the two sides (chambers) of the pump. In some applications this results in improved efficiency.

DETAILED DESCRIPTION OF THE SPECIFIC EMBODIMENTS

Figure 1:
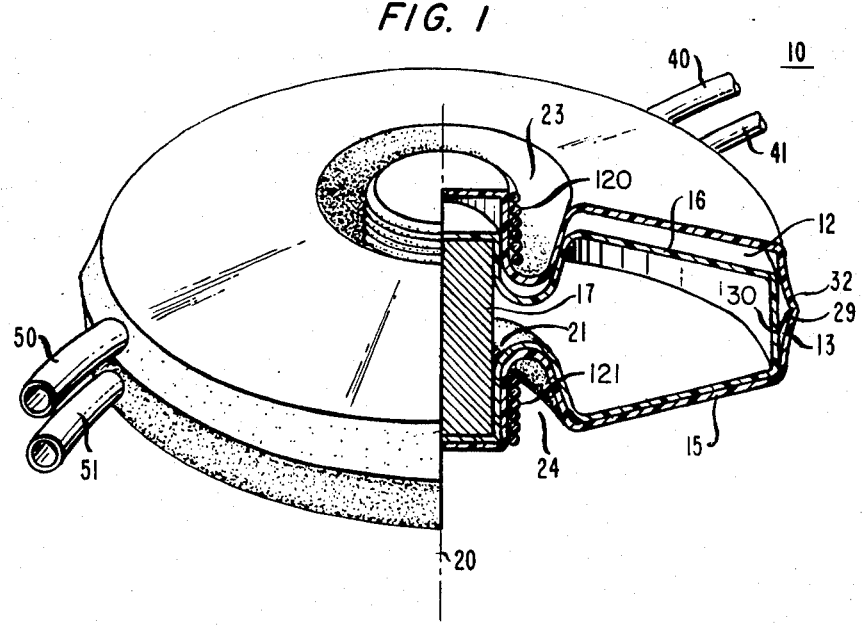
FIG. 1 is a schematic plan view of a diaphragm pump arrangement in accordance with this invention.

FIG. 1 shows a projection view of a diaphragm pump 10 in accordance with one embodiment of this invention. The pump comprises first and second chambers 12 and 13, each of which is generally annular in shape.

Figure 2:
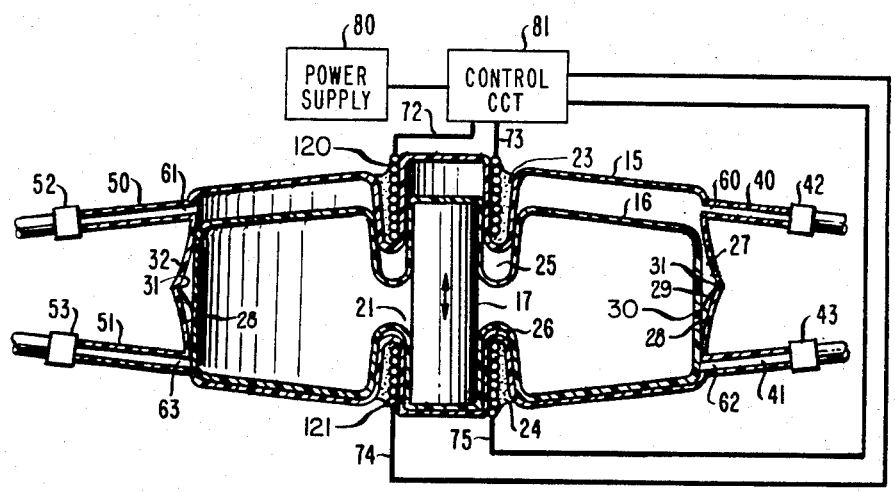
FIG. 2 is a side cross-sectional view of the pump of FIG. 1.
Figure 3:
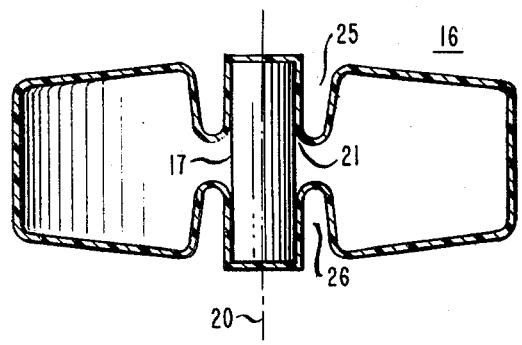
FIG. 3 is a side cross-sectional view of the piston of the pump shown in FIG. 1.

As shown in FIGS. 1 and 2, the shapes of the first and second chambers are defined by the housing 15 for the pump, the piston 16, and magnetic plunger 17. As shown in FIG. 3, piston 16 is formed in the general shape of a hollow donut as shown in cross section. The piston includes a center section 21 into which plunger 17 is secured as shown in FIG. 2. Any movement of plunger 17 along axis 20 consequently results in vertical displacement of the piston. The magnetic piston is free to move up and down as viewed in FIG. 2 along imaginary axis 20, as is explained more fully hereinafter.

Housing 15 has a shape which corresponds to that of piston 16. In addition, housing 15 includes central annular depressions 23 and 24 on the top and bottom surfaces as viewed in FIGS. 1 and 2. It can be seen that piston 16 also includes central annular depressions 25 and 26 respectively. The depressions in the housing and pistons are designed to allow the piston and the housing to mate closely when the piston is displaced. Housing 15 also includes conformal wall portions 27 and 28 with which piston 16 mates closely when plunger 17 is displaced. Reciprocal movement of plunger 17 along axis 20 consequently seats piston 16 into the conformal shape formed in housing 15 by central recess 23 and conformal wall portion 27 on the top surface of the housing as viewed in FIG. 2 and by central recess 24 and conformal wall portion 28 on the bottom surface as therein viewed.

A permeable and flexible diaphragm 29 completes the separation of chambers 12 and 13 one from the other. The diaphragm is in the form of an annulus and is secured about piston 16 at center line 30. The exterior periphery of the diaphragm is secured to a mean circular line 31 about the exterior side wall 32 of housing 15. Diaphragm 29 is dimensioned to permit a snug fit along conformal wall portions 27 and 28 of wall 32 when plunger 17 is displaced upward or downward respectively. Conformal wall portions 27 and 28 are equipped with openings (ports) 60 and 61 and 62 and 63 respectively, as shown in FIG. 2, for access and egress of fluid from the chambers.

Fluid access to chambers 12 and 13 is provided by conduits 40 and 41. The conduits include check valves 42 and 43 which allow fluids to be drawn into the corresponding chambers 12 and 13 respectively when one of those chambers is being enlarged by the movement of plunger 17. Of course, only one of check valves 42 or 43 remains open during movement of the plunger 17 because only one of chambers 12 or 13 is being enlarged. The other is being reduced in size, resulting in the compression of fluid in that chamber and the forcing of the corresponding check valve to close.

Chambers 12 and 13 also have exit conduits 50 and 51 with check valves 52 and 53 respectively. The movement of plunger 17 to expand chamber 13, for example, opens check valve 43 but closes check valve 53. Thus, when the chamber 13 expands, fluid enters chamber 13 through conduit 41 by means of open check valve 43. When chamber 13 is reduced in size, fluid is forced out through conduit 51 via the then open check valve 53, and check valve 43 is closed by the compressed fluid. The operation with respect to chamber 12 is exactly the same, fluid entering the chamber through conduit 40 and check valve 42 and exiting through conduit 50 and check valve 52, the operations taking place for the two chambers 12 and 13 during alternate strokes of piston 16.

The reciprocal changes in the volume of chambers 12 and 13 are caused by the displacement of plunger 17 to which piston 16 is secured. The displacement of plunger 17 is caused electromagnetically in the illustrative embodiment herein. To this end, central recesses 23 and 24 of housing 15 include solenoid coils 120 and 121 to which electrical access is provided via electrical conductors 72 and 73 and 74 and 75 respectively.

Power is supplied by power supply 80 under the control of control circuit 81. Control circuit 81 is adapted in the illustrative embodiment so that the coils operate in tandem. That is to say, control circuit 81 induces currents, in each of the coils with polarities so that when one coil pushes plunger 17, the other pulls. The control circuit 81 causes successive reversals of the polarity of the current in the coils, and each polarity reversal accordingly reverses the coils on plunger 17. Thus the plunger 17 is made to reciprocate.

Housing 15 includes conformal wall portions 27 and 28 of side wall 32 against which diaphragm 29 seats when plunger 17 is displaced upward or downward along axis 20 as has been stated hereinbefore. Such an arrangement minimizes residual volume in the chamber on the compression side of the diaphragm when the plunger is in an extreme position, and maximizes the residual pumping efficiency of the piston in the event that the diaphragm becomes cracked or ruptured.

If we take the sidewall 32 of the housing as having a vertical dimension d along axis 20, and if we take the sidewall of piston 16 as having a smaller vertical dimension h, we can restrain the travel of piston 16 along axis 20 to a distance K=d-h. Consequently, we can design the pump to avoid stresses on the diaphragm. It should be clear from the drawing that the diaphragm has a radial dimension greater than the separation between the housing 15 and the piston 16, so as to allow the diaphragm to seat smoothly against the conformal walls when the plunger has travelled to an extreme position.

If the pump of FIGS. 1–3 is to be used as an artificial heart, the chambers 12 and 13 are operative as the first and second ventricals of the heart. The right ventrical of the heart pumps blood to the lungs and the left ventrical pumps blood through the entire body. The heart thus comprises two pumps, the pumps expanding and filling and then contracting and emptying at approximately the same time. The expand and fill phase is called the diastole and the contracting and pumping phase is called the systole. Prior art "total" artificial hearts have required two separate pumps, each with two chambers and each filling only one chamber with blood. The other chamber in each pump has been filled with gas which needs venting or a surge chamber, or with a fluid (other than blood). In each instance a totally sealed unit has been hard to obtain.

In accordance with a total artificial heart embodiment herein, both chambers of a single diaphragm pump are occupied by blood, and blood is pumped from the body to the lungs during one phase and pumped from the lungs to the body in another phase. While one chamber contracts and empties, the other expands and fills so that the terms diastole and systole are obscured, the artificial heart herein being characterized by a double-rate heart beat. Nevertheless, the unit can be sealed totally and no venting is required.

Alternatively, the two pumping chambers may be connected in series, the outlet of one chamber being connected to the inlet of the second chamber, to obtain a single action pump or artificial heart assist pump if desired.

Figure 4:
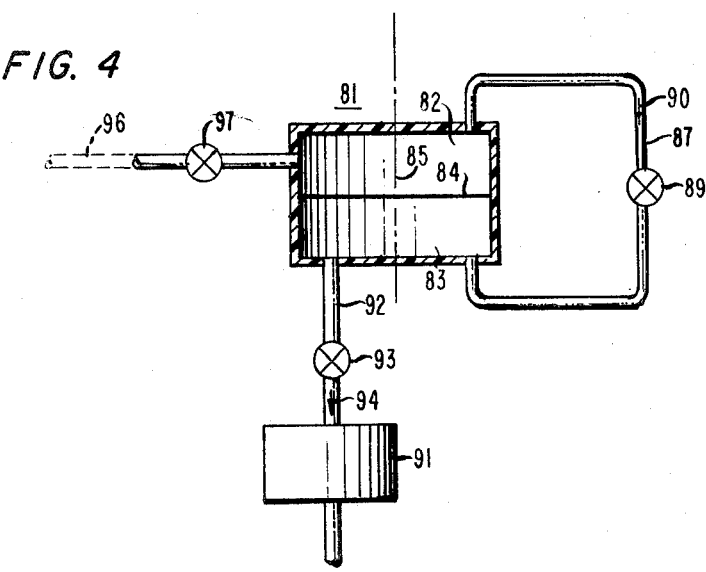
FIGS. 4 and 5 are schematic views of the interconnections of pumps with fluid conduits for the circulation of fluids such as blood in accordance with other embodiments of this invention.

FIG. 4 shows one such arrangement where pump 81 includes first and second chambers 82 and 83 with element 84 movable, up and down as viewed, along axis 85. Chambers 82 and 83 are connected by conduit 87. Conduit 87 includes check valve arrangement 89 adapted to permit blood to move from chamber 82 to chamber 83 as indicated by arrow 90. Block 91 indicates the arterial system of the human body and can be seen to be connected to chamber 83 by conduit 92. Conduit 92 includes a check valve arrangement 93 adapted to permit blood to flow only into the arterial system represented by block 91 as indicated by arrow 94. Broken lines 96 indicate the veins of a human circulatory system and are shown connected to chamber 82. A check valve arrangement 97 is included at the inlet to chamber 82 to permit blood to flow only into chamber 82.

In operation, the movement of element 84 up and down along axis 85 in one complete cycle of operation causes a pumping action in the arterial system and the advancement of the blood in chamber 82 to chamber 83. The replenishment from the veins occurs as chamber 82 enlarges.

It is to be emphasized that chambers 82 and 83 are interconnected by conduit 87 in a manner to permit fluid movement to chamber 83. Such an interconnection is considered a significant departure from prior art teaching.

Figure 5:
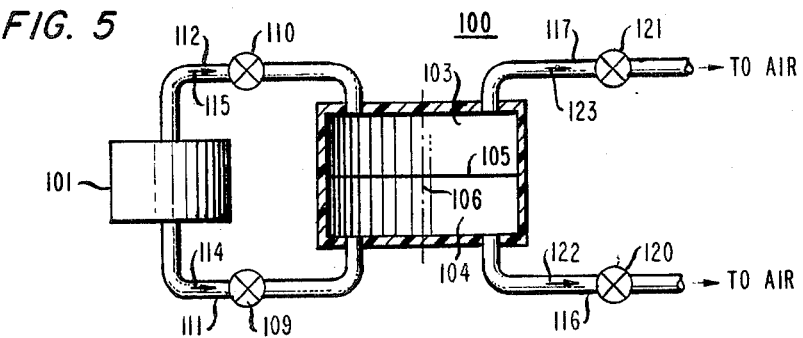

FIG. 5 shows an arrangement where a pump 100 is adapted to evacuate a chamber 101. The pump again has two chambers 103 and 104. Element 105 is adapted to move up and down as viewed along axis 106 alternately evacuating air from the chambers and thus from chamber 101. Check valves arrangements 109 and 110 are adapted to permit flow of air in conduits 111 and 112 only as indicated by arrows 114 and 115 when the volume of the associated chamber of pump 100 is being expanded. Chambers 103 and 104 are vented to air by conduits 116 and 117 respectively. Conduits 116 and 117 include check valves arrangements 120 and 121 respectively. The check valve arrangements are adapted to permit air to flow only as indicated by arrows 122 and 123.

Displacement of element 105 in either direction along axis 106 causes evacuation of chamber 101 as is clear from the Figure. Thus, the energy expended to move element 105 through one cycle of operation results in a double cycle of evacuation of chamber 101 leading to a relatively efficient operation. The interconnection of chamber 101 to both chambers of the pump and the adaption of the check valves to permit evacuation during each half cycle of the pump is also considered to be a significant departure from prior art teaching.

It should be clear from FIGS. 4 and 5 that other than diaphragm pumps can be used in accordance with this invention. Moveover, it should be clear that any of the various arrangements shown can be used to evacuate or pressurize depending on the check valve arrangements. For example, a change of the check value arrangement in the embodiment of FIG. 5 to permit air to enter all the conduits would produce a hard tire pump which would pressurize on both half cycles of operation. In this instance the controlled environment chamber (the tire) would be connected to a merge conduit for attachment to the tire.

For use of pump arrangements as described herein for total heart replacement or heart assistance, a portable power supply is necessary. Such a supply is well known in the art, as is the interconnection of such a supply to the implant. For example, in the present case, to the coils designated 120 and 121 in FIGS. 1 and 2, conductors 72, 73, 74 and 75 provide electrical access as described hereinbefore. Materials for the various elements of the pump, the power supply and the interconnections are all well known in the art.

The piston itself also is particularly well adapted for use in artificial heart applications. The fact that the piston is hollow allows for a light weight design while permitting the chamber volumes to match the volumes of the ventrical of the human heart. Moveover, the piston may be filled, for example, with helium to lighten the weight of the pump further. Further, recesses 23 and 24 of housing 15 may be filled with a suitable material such as Teflon for use with implants to prevent body fluids from contacting coils 120 and 121.

What is claimed is:

1. A pump including:
   a housing:
   a diaphragm having a hollow rigid center portion and a flexible, annular-shaped membrane portion having its periphery attached to the housing at a center line thereof so as to divide said housing into first and second isolated pump chambers;
   means for moving the diaphragm in a push-pull manner to enlarge and then reduce the volume of each of said pump chambers alternately; and
   an entrance and an exit conduit connected to each of said pump chambers, said conduits including check valve arrangements for permitting a fluid medium to enter said entrance conduit and to exit said exit conduit when the associated chamber is enlarged and reduced in volume respectively.

2. A pump arrangement in accordance with claim 1 wherein said hollow rigid center portion includes electromagnetic means for moving said diaphragm within said housing.

3. A pump arrangement in accordance with claim 2 wherein said housing includes first and second broad faces, said faces having centrally disposed annular depressions for containing said electromagnetic means.

4. A pump arrangement in accordance with claim 3 in which each of said broad faces has a shape which conforms to that of said hollow rigid center portion of said diaphragm.

5. A diaphragm pump comprising a hollow housing having contoured first and second surfaces separated a distance x by a peripheral side wall, said housing containing a diaphragm separating said housing into first and second chambers; means for moving said diaphragm in a push-pull manner to enlarge and reduce the volumes of said chambers alternately, said diaphragm being characterized by a hollow rigid center portion and an annular-shaped membrane connected at its periphery to said housing at a center line thereof, said peripheral wall including first and second conformal walls, said diaphragm being adapted to seat against said conformal walls when moved to first and second extreme positions respectively, and means for moving said diaphragm from one of said extreme positions to another.

6. A diaphragm pump in accordance with claim 5 wherein said means for moving said diaphragm includes a magnetic rod and said housing includes first and second recesses bearing electric coil means for moving said rod when energized, said annular recesses being of sufficient depth y and said rod being of sufficient length z such that said diaphragm is displaced a distance $x-z < y$.

* * * * *